United States Patent [19]
Reiman

[11] 3,973,559
[45] Aug. 10, 1976

[54] CHILDREN'S CORRECTIVE FOOT SPLINT

[76] Inventor: Reuben H. Reiman, 17 Beverly Road, Port Washington, N.Y. 11050

[22] Filed: June 6, 1975

[21] Appl. No.: 584,252

Related U.S. Application Data

[63] Continuation-in-part of Ser. No. 497,196, Aug. 14, 1974, Pat. No. 3,910,267.

[52] U.S. Cl. .............................. 128/80 A; 128/80 J
[51] Int. Cl.² ........................................... A61F 3/00
[58] Field of Search ............. 128/80 A, 80 R, 80 J, 128/80 B, 83, 87

[56] References Cited
UNITED STATES PATENTS

| | | | |
|---|---|---|---|
| 2,702,542 | 2/1955 | Gessel | 128/80 A |
| 3,209,749 | 10/1965 | Walker | 128/80 J |
| 3,265,063 | 8/1966 | Friedman | 128/80 A |
| 3,777,747 | 12/1973 | Friedman | 128/80 A |
| 3,812,850 | 5/1974 | Reiman | 128/80 A |

OTHER PUBLICATIONS

"A Universal Joint Club Foot Splint," by A. Gibson, The Journal of Bone and Joint Surgery, vol. 36A, No. 3, June 1954, pp. 658, 659.

*Primary Examiner*—John D. Yasko
*Attorney, Agent, or Firm*—Bauer, Amer & King

[57] ABSTRACT

The invention relates to a foot splint for correcting abnormalities and foot deformations that are sometimes found in newborn and yound children. It includes relatively fixed, angularly related foot supports, each having a wall about the heel and extending continuously along a length of each support to apply a medial restraint and lateral support to the inner surface of the foot and heel while strap means retains each foot on its respective support to prevent displacement of the heel as well as medial displacement of the forefoot relative to its respective support.

4 Claims, 6 Drawing Figures

U.S. Patent   Aug. 10, 1976   3,973,559
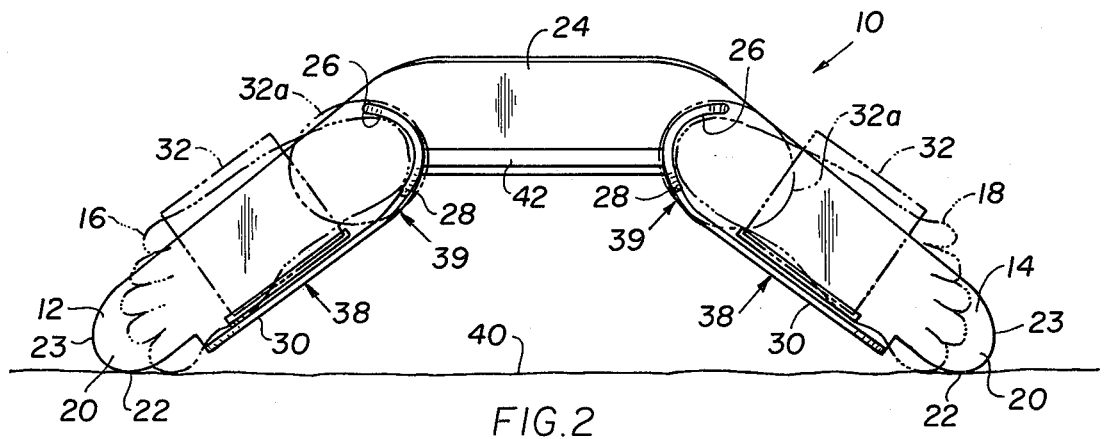
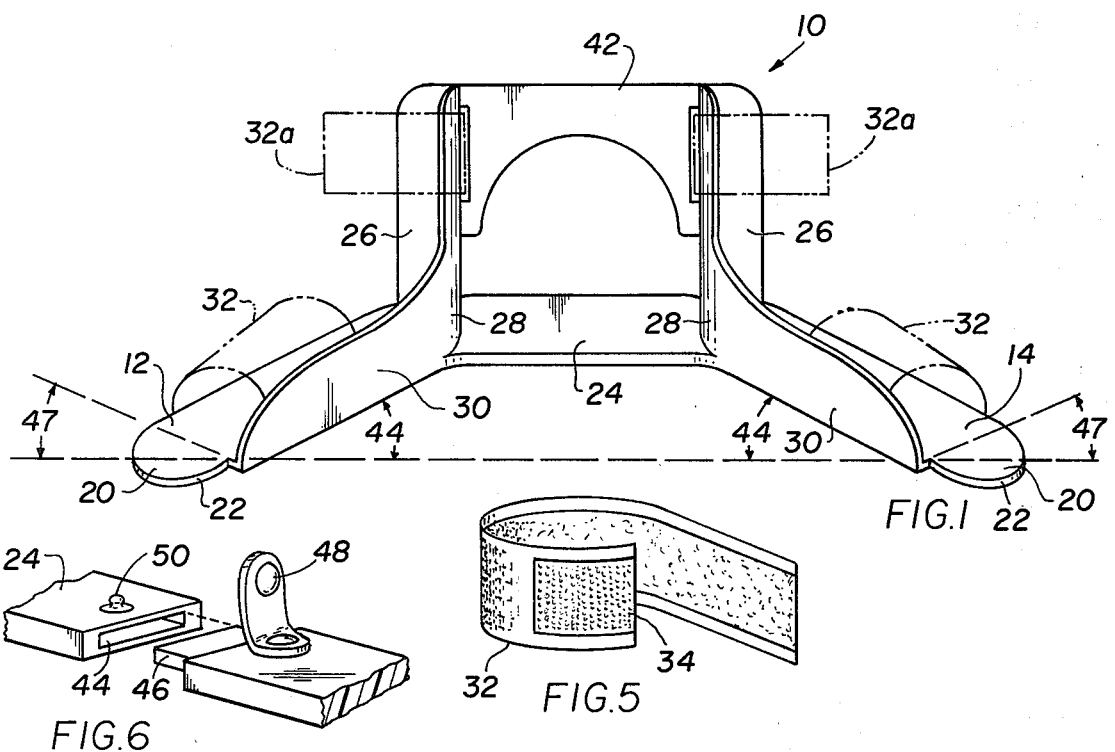
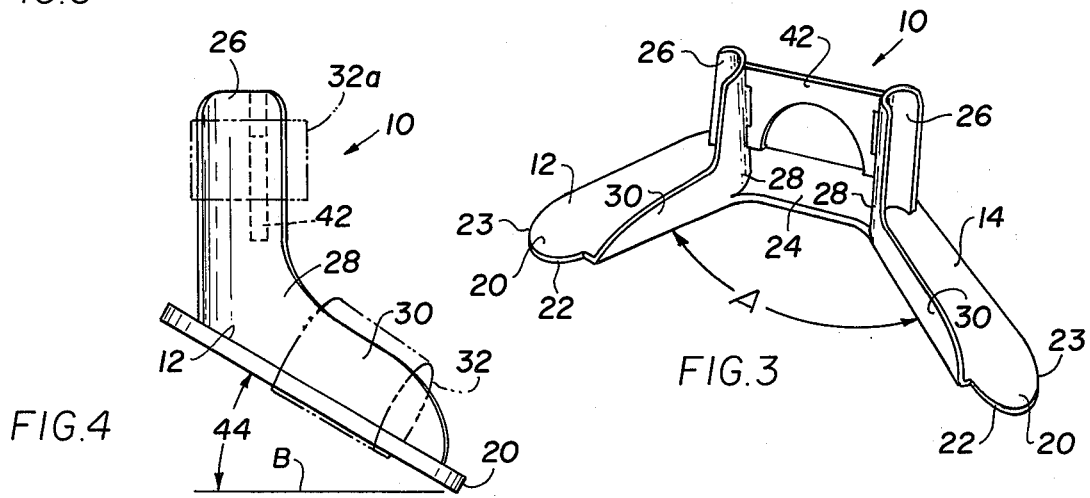

CHILDREN'S CORRECTIVE FOOT SPLINT

The general problems treated by the present invention and examples of prior art were discussed at length in applicant's U.S. Pat. No. 3,812,850 and in application Ser. No. 497,196 filed Aug. 14, 1974, now U.S. Pat. No. 3,910,267 of which the present application is a Continuation-In-Part.

BACKGROUND OF THE INVENTION

This invention relates to a foot splint for attachment to the feet of children for correcting such abnormalities and deformations as toe-in, "pigeon-toe-in", club feet, bowlegs and the like.

SUMMARY OF THE INVENTION

Although the objects of applicant's prior patent, as set forth above, are still the objectives of the present application, it is also an object of the present application to take advantage of the physical forces exerted by a child suffering from the aforementioned abnormalities and deformations and to utilize the same to aid in the correction of such undesired conditions more effectively, more rapidly and more inexpensively than was heretofore enabled by prior art structures, all without the requirement of unusual training or skills.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

FIG. 1 is a perspective view taken at an angle of the front and top of a foot splint constructed according to the invention;

FIG. 2 is a top view;

FIG. 3 is a perspective view similar to FIG. 1 but taken at an angle thereto;

FIG. 4 is a side view;

FIG. 5 is a perspective view of a strap means; and

FIG. 6 is a partial view of a modification of the foot splint.

Referring to the drawing, the children's corrective foot splint, illustrated in FIGS. 1, 2, 3 and 4, is generally identified by the numeral 10. It comprises a pair of foot support members 12 and 14 that are substantially planar at their upper surfaces to facilitate the positioning of the sole of a child's foot on each of such respective members. The support member 12 will accommodate the right foot of the child while the support member 14 will accommodate the left foot of the child. Each of the support members 12 and 14 is substantially identical to the other. They extend for a distance at least and greater than the full length of the foot of the child to be positioned thereon and may be substantially equal to, but preferably less in width than the sole of the child's foot.

This is illustrated more clearly in FIG. 2 wherein the left and right feet respectively, shown in broken lines, are positioned on their respective foot supports 12 and 14. It will be noted that the right foot 16 and the left foot 18 of a child using the splint 10 are substantially shorter in length than that of each of the foot support members on which they are positioned and substantially greater in width than such foot support members for a purpose to be described. For convenience, each of the foot support members 12 and 14 is provided with a toe portion that is identified by the numeral 20. Each toe portion 20 is rounded on its inner portion or side as at 22 while the opposite side 23 of the toe portion 20 may be smoothly finished in any desired manner.

The foot support members 12 and 14 are generally fixed in a diverging angular relationship approximating an included angle of about 90° as shown at A in FIG. 3. To achieve the desired normal angular diverging relationship of the feet of a child, such foot support members 12 and 14 are retained in their generally fixed spaced relationship by a central connecting means or portion 24. In the embodiment shown in FIGS. 1 and 2, the connecting means 24 is formed unitary and coextensive with the foot support members 12 and 14.

Mounted on and forming an integral construction with each of the foot support members 12 and 14 is a respective support sometimes hereinafter referred to as a heel support member 26. Each heel support member 26 has its major portion 28 curved to approximate shape of the heel and extending along a lengthwise inner edge adjacent or bordering the rear of each of the foot support members 12 and 14 so as to provide a wall against which the heel of a child's foot may be comfortably butted and engaged. As a coincidental and added attribute of the heel support members 26, each has a contiguous and coextensive medial wall 30 directed along and for a substantial length of each of their respective foot support members 12 and 14.

Although the major portion or extent 28 applies a medial restraint to and against the displacement of the heel of the child's foot relative to the support, the minor portion 30 does enable the individual applying the foot splint 10 to the feet of a child to properly position the heel of each foot on the respective foot support surfaces 12 and 14 snugly and properly against the major medial support surface 28. This may be seen more clearly in FIG. 2 wherein the broken lines, illustrating the feet 16 and 18, are shown to be in position against the surfaces 28 and 30 of the heel support members 26. The lengthwise extent of the surfaces 30 are sufficient to continue to and along the lower medial portion of each foot support 12 and 14 and therebeyond the metatarsus and to the forefoot.

Mounted intermediate the heel portion of each support member 12 and 14 and the toe portion 20 thereof is an adjustable releasable strap securing means 32 more fully shown in FIG. 5. In practice, each such strap is provided with a VELCRO fastener 34, although a buckle or other fastening means may be used to enable the strap to be adjusted about the instep of the child's foot to inhibit medial rotation of the forefoot. Thus, in practice, when the feet 16 and 18 of the child are positioned flat against the upper surfaces of the foot support members 12 and 14, and abutted against the medial side walls 30, and positioned against the heel portion 28 of each heel support member 26, the strap 32 is then wrapped about the instep of the foot as illustrated in broken lines in FIGS. 1 and 2 and as shown in the intermediate position of FIG. 4.

When the strap 32 is so secured about the forefoot of the child's foot, the foot is held firmly, but not uncomfortably, against the upper surface of each of the foot supports 12 and 14 buttressed against the medial foot support walls 30. At the same time, the heel of each such foot is forcibly urged against and into engagement with their respective restraining surfaces 28 of the heel support members 26. To understand this better, each strap 32 provides a restraint to each foot from rotation relative to its support 12 or 14 and a lateral force 38 that is medially directed against the outer surface of each foot to move and retain the same in the direction of and restrained against the inner surface of wall 30 as shown in FIG. 2.

The medial inward restraint of the strap 32 counters and is opposed to the lateral outward directed force that is exerted against each foot by the surfaces 28, such as is depicted by the force arrows 39 in FIG. 2. The application of the inward forces applied to the foot at the straps 32 and the outward forces applied to the inner portion of the heel of each foot as demonstrated by the arrows 39 at the surfaces 28 should be apparent to those skilled in the art. A child who suffers from a toe-in abnormality or a bowleg deformation or other similar condition normally tends to toe in at the toes and outward at the heels.

By positioning the heel of each foot against the respective surface 28 by the heel restraining strap 32a, the heel is held against such surface 28. This opposes the tendency of the child's heel to move outward away from the surface 28. At the same time the forces applied to the child's forefoot at the medial or inner wall 30, aided by the foot strap 32, such as in the direction of the arrows 38, counter that force that is normally present in the child's normally inwardly directed toed feet. Hence, the forces 38 and 39 aid and add to each other and, in like manner, are opposed to the abnormal tendency of rotation of the child's feet that is desired to be and must be corrected.

By so positioning each of the feet of the child against the surfaces 28 and strapping the same in place against the foot support members 12 and 14 by the straps 32a, the outward forces 39 and 38 tend to counteract the abnormal forces that are present in a child's feet that create the abnormality or deformation that must be corrected. Once the child's foot is strapped against the foot support members 12 and 14 in the manner described, the application of the forces 38 and 39 will cause the legs and the feet to rotate about the heel of the child's feet. Because each heel is fixed and held to its support 28, it cannot shift away from the support 28, but must rotate about an imaginary axis extending through the restrained heel and the child's leg. This rotation causes the feet to assume the proper divergent angle "A" corresponding to that of the foot support surfaces 12 and 14.

In the illustration of FIG. 2, it will be noted that the large toe of each foot is shown engaged against a surface such as the surface of a bed or mattress 40. As a consequence, a further torqueing force is applied to the toes of each of the feet 16 and 18 causing them to further flex and rotate outward in the direction of the force applying arrows 38, thereby also tending to straighten and correct the abnormality or deformation.

Although the substantially planar foot support members 12 and 14 may be formed as a unitary continuous element made of any rigid or mildly flexible material, if desired, the planar foot support members may be made separable at the central connection means or portion 24. By so doing, each foot 16 and 18 may be more easily fixed individually to its respective foot support 12 and 14. Then, after being so fixed, the two support members 12 and 14 may be secured together in a manner to be described. The heels 26 may be further secured together by a bridge-like strut 42.

In this regard, reference is made to FIG. 6 wherein the connecting portion 24 is illustrated. One side of the connecting portion 24 may be provided with an internal hole 44 while the other side may be provided with an engaging and positioning tongue 46. When the tongue is inserted into the hole 44, the two parts of the central portion 24 are aligned and connected together with each other. The connection is made complete by a releasable fastener 48 engaging with a fastener button 50. The releasable engagement between the fastener 48 and the button 50 enables each of the foot support members 12 and 14 to be connected together for conjoint use in the arrangement as shown in FIGS. 1 and 2. However, for convenience of application to the feet of a child, the same may be separable from each other by disengaging the fastener 48 from the button 50 and separating the two foot support members from each other. In like manner to that described, the strut 42 may be separably connected as described with respect to portion 24.

The natural tendency of the feet 16 and 18 afflicted with the deformations or abnormalities discussed previously is for the child's heels to rotate laterally outward and the toes laterally inward toward each other. That is to say, the abnormal right foot 16 tends to rotate counterclockwise while the left foot 18 tends to rotate clockwise. Thus, when each of these deformed feet are strapped to their respective support surfaces 12 and 14 and abutted against their medial support surfaces 28, the surfaces 28 and lateral supports 30 counteract the normal rotational forces effected by the anatomy of the feet to further aid in the counteracting of the natural tendency of the feet to rotate inward toward each other at the toes.

To aid in the correction of the feet, the foot support members 12 and 14 are made longer in length than the foot to be supported thereon as is illustrated in FIG. 2. Although the feet 16 and 18 illustrated in FIG. 2 are shown wider in width than that of their respective support surfaces 12 and 14, in the event the feet are approximately the same width as their respective support members, the rounded ends 22 of each longer foot support member 12 and 14 will engage against the bed or mattress surface 40 in the same manner as the toe of each foot 16 and 18 is shown to be in engagement with such surface 40. During such engagement, there is an outward rotation or counteracting torqueing force applied, either to the toe of the foot directly as shown in FIG. 2 or to the rounded portion 22 of the respective foot support members 12 and 14. This produces an outward rotating force against the abnormal foot that is applied to the heel of each foot. Because the heels are restrained by straps 32a to abut their supports 28, a lateral counter force 39 is applied thereto causing the heel to remain fixed but permitting the forefoot to rotate properly in the direction of arrow 38 about the fixed heel. This rotative motion about the fixed heel tends to straighten and correct the abnormality.

In this manner, advantage is taken of the counteracting torqueing forces that may be applied to the feet of the child when the child is lying prone on a bed or mattress or other surface. Such torqueing forces tend to correct the abnormality or deformation each time the child moves because the rocking motion that occurs at the rounded ends 22 tends to rotate and toe outward each of the child's feet.

Referring to the illustration in FIGS. 1 and 4, it will be noted that the planar foot supports 12 and 14 are tilted downward at an angle 44 relative to the vertically disposed heel support members 26 and with respect to a horizontal plane "B". The downward tilted angle of the supports 12 and 14 may be referred to as the "natural carrying angle" of the feet with respect to the legs. Thus, when the child is being held or carried about the waist and the legs and feet hang downward, the feet tend normally to assume a downward tilted "carrying angle" of approximately 20° to 25°. This enables the child's feet, supported on the respective planar supports, to be supported in their natural dropped or "carrying angle."

The planar supports 12 and 14 further provide an everted means by being provided with an eversion angle 47 of approximately 10°. The eversion angle 47 enables the inside of the foot to be positioned and to ride naturally against the minor medial wall support or portion 30 to be supported thereby and thereagainst. By lowering the inside of the foot with respect to the outside of the foot and further, by providing for the natural tilted carrying angle of the supports 12 and 14, genu valgum or knock knees are averted during the correction of the foot abnormality. The ability to rotate the foot about the fixed heel as previously described herein and further, by providing for the natural carrying angle and eversion means, the tendency toward knock knees, which has been experienced in prior art correctional splints, is now avoided and obviated.

Those skilled in the art will readily recognize that the present invention takes advantage of the natural tendency of the feet to assume their abnormality or deformation and thus utilizes these abnormal and deforming forces to counteract the abnormality or deformation and to straighten the feet or correct the undesired condition.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A foot splint for attachment to the feet of a child for correcting toe-in and related abnormalities comprising a substantially planar support for the full length of each foot,
    a heel support unitary with each of said foot supports,
    said heel supports extending for a portion of the length of its respective foot support at a medial inner portion thereof and being curved about the heel of its respective foot support for a portion thereof delineating the heel of its respective foot support,
    a wall contiguous with each planar support to extend upward therefrom beginning from the forefoot supporting portion of said planar support and continuing rearward therealong toward and as a contiguous extension of said heel support,
    means rigidly connecting said foot supports against relative movement,
    each said heel support including means extending upward from its respective foot support for a height sufficient to apply a restraint to and against the relative movement of the heel of a foot positioned thereagainst while permitting rotation of the foot at the heel so restrained,
    each foot support being disposed at an eversion angle wherein the inside of each foot support is lowered relative to the outside thereof,
    and strap means on each of said foot supports to engage the forefoot of a foot positioned on a respective foot support to inhibit the medial rotation of the forefoot relative to its respective foot support and applying a lateral outward force thereto to rotate the foot about the restrained heel of the foot.

2. A foot splint as in claim 1,
    said connecting means including means operable to release each of said foot supports from their connected fixed diverging angular relation and to connect the same together in said fixed diverging angular relation.

3. A foot splint as in claim 2,
    said foot supports being greater in length and lesser in width than that of a foot to be positioned thereon to enable said instep strap means to apply its lateral outward force to the foot.

4. A foot splint as in claim 1,
    each of said foot supports being tilted downward to conform to the natural carrying angle of a foot positioned on said foot supports and with respect to the leg thereof.

* * * * *